United States Patent [19]

Fishgoyt

[11] Patent Number: 4,913,165

[45] Date of Patent: Apr. 3, 1990

[54] UNDERWATER EARDRUM PROTECTOR

[75] Inventor: Michael Fishgoyt, 654 Water St., Apt. 4A, New York, N.Y. 10002

[73] Assignees: Michael Fishgoyt, New York; Elena Heimur, Staten Island, both of N.Y.

[21] Appl. No.: 384,405

[22] Filed: Jul. 24, 1989

[51] Int. Cl.$^4$ .............................................. A61F 11/02
[52] U.S. Cl. ...................................... 128/865; 181/130
[58] Field of Search ............... 128/865, 864, 866, 867, 128/868; 181/130

[56] References Cited

U.S. PATENT DOCUMENTS

| | | | |
|---|---|---|---|
| 2,876,767 | 3/1959 | Wasserman | 128/865 |
| 3,110,356 | 11/1963 | Mendelson | 181/130 |
| 3,505,999 | 4/1970 | Harvey et al. | 128/865 |
| 3,602,654 | 8/1971 | Victoreen | 181/135 |
| 4,006,796 | 2/1977 | Coehorst | 181/130 |
| 4,060,080 | 11/1977 | Akiyama | 128/865 |
| 4,299,237 | 11/1981 | Foti | 128/742 |
| 4,406,282 | 9/1983 | Parker et al. | 128/865 |

Primary Examiner—Robert A. Hafer
Assistant Examiner—Lynda M. Cofsky
Attorney, Agent, or Firm—Andrew S. Langsam

[57] ABSTRACT

An underwater eardrum protector for use in underwater diving by a person having a perforated eardrum includes an inflatable bladder insertable in an ear canal of the person; a tube for supplying a non-compressible fluid to the bladder so as to inflate the same; a housing fluidly connecting the bladder to the tube; and a pump which supplies the non-compressible fluid to the tube, the pump including a cylinder having an inner wall, a piston slidable in the cylinder so as to define a variable volume chamber with the inner wall of the cylinder, the chamber being in fluid communication with the tube, O-rings connected with the piston for providing a fluid seal between the piston and the inner wall of the cylinder so as to seal the variable volume chamber, and a piston rod for slidably moving the piston in the cylinder so as to reduce the volume of the chamber and force the non-compressible fluid in the chamber through the tube and into the bladder, the piston rod being connected with the piston in a freely rotatable manner and being threadedly connected with the cylinder.

32 Claims, 2 Drawing Sheets

UNDERWATER EARDRUM PROTECTOR

BACKGROUND OF THE INVENTION AND DESCRIPTION OF THE PRIOR ART

The present invention is generally directed to underwater diving, and more particularly, is directed to an underwater eardrum protector which protects scuba divers who have perforated eardrums. The device can also be used by individuals engaged in surface water sports (not more than about 30 feet of water depth) even if those individuals have healthy eardrums. The present invention serves to block water from entering into the auditory canal, a desirable result for individuals with healthy and damaged eardrums. As will be more fully explained hereinafter, the present invention should not be used by individuals with healthy eardrums at great water depths.

Current medical practice dictates that scuba divers should not dive to too great a depth if they have perforated eardrums, that is, ruptures or tears in their eardrums. This is because of the high water pressure which results in penetration by the water into the ear, causing permanent inner ear damage.

U.S. Pat. No. 4,406,282 to Parker et al discloses an earplug for an underwater diver. Specifically, the earplug includes a tubular bladder which is closed at its inner end and which is constructed of a soft, elastic-like material. Optionally, a set of filaments can be molded into the elastic-like material to allow radial expansion and inhibit lengthwise or axial expansion. This earplug is inserted into the ear and establishes an air pocket between the eardrum membrane and the end of the device. The air within the air pocket, as a result of the increased pressure on the eardrum due to deep diving in water, causes the flexible bladder to move, (See FIG. 5 thereof) to ensure contact between device and the middle ear's auditory canal.

The device of the '282 patent is not suitable for use by a diver having a puncture or tear in the eardrum. The present invention, in contrast, is primarily useful by those water divers having preexisting punctures or tears in their eardrum membranes. Also, in underwater diving situations, it is desirable that the user, as mentioned, having a preexisting eardrum puncture, be able to vary the pressure by the tubular bladder in the ear to a pressure different from that provided inclusively as a result of water pressure to ensure contact between the device and the auditory canal.

U.S. Pat. No. 3,505,999 to Harvey et al discloses an earplug having an expandable bag or balloon secured to a tube for selective insertion into the ear. A syringe or pump-like device serves to adjust the size of the balloon by adjusting the pressure on the fluid contained within the syringe and connecting tube. The pump-like device includes a cylinder having a fluid therein and a piston axially slidable within the cylinder for forcing the fluid through the tubing and into the expandable bag. A piston rod is fixedly connected with the piston for slidably moving the same within the cylinder.

In order to retain the piston in a desired depressed position, O-rings provide a tight fit between the piston and the interior wall of the cylinder. Accordingly, once the piston is moved to a depressed condition, thereby forcing the fluid from the cylinder through the hollow tube and into the expandable bag, and since the O-rings of the piston are in sufficiently tight frictional engagement with the interior wall of the cylinder, the piston will remain in such position. However, such tight frictional engagement between the piston and the cylinder so as to maintain the piston in its desired position causes extreme wear on the O-rings, thereby resulting in early failure of the device. Further, when performing underwater dives, the pressure within the ear may be sufficiently great to slidably move the piston out of the cylinder. The reason that no securing means is provided with this earplug is that it is designed to give protection against industrial noises and the like, that is, at atmospheric pressure. It is not intended for use at elevated pressures such as deep water diving.

U.S. Pat. No. 3,110,356 to Mendelson teaches an earplug having an ear insert member portion which has a canal or channel member and a flexible member in surrounding relation thereto. A sealed space is provided and bounded on the outside by the flexible member and on the inside by the channel member. A reservoir of liquid is provided for adjusting the size of the sealed space to thereby hold the earplug in position. Specifically, a tube connects the sealed space with the interior of a cylinder of the reservoir. A piston or plunger is slidably positioned within the cylinder. There is no specific description, however, of the relationship between the plunger rod and the cylinder of the reservoir. It appears from the drawing of FIG. 2 that the plunger rod is threadedly engaged with the cylinder. This would allow for the plunger to move in both directions as the turning screw is alternatively rotated in both directions. However, with such a relationship, rotation of the plunger rod to axially move the plunger or piston within the cylinder also results in rotation of the plunger itself. In the case where no O-ring is provided, a sufficiently tight fluid sealing arrangement cannot be provided, particularly in underwater diving situations. In the case where an O-ring is provided between the plunger and inner cylinder wall, there is an axial and rotational movement of the O-ring against the inner cylinder wall, resulting in relatively quick wear of the O-ring, and possibly early failure of the device, which can have disastrous consequences in deep underwater diving situations. In any event, the earplug of the 356 patent is designed specifically for above water, that is, atmospheric pressure, situations.

U.S. Pat. No. 2,876,767 to Wasserman discloses an earplug with an inflatable bladder which adapts itself to the contour of the ear canal. A syringe serves to adjustably provide pressure through a tube positioned within the interior of the inflatable bladder. However, there is no means to secure the plunger in a desired depressed position. Apparently, this occurs by means of friction between the plunger and the inner walls of the bore within which it rides.

Other similar, but less pertinent, devices are disclosed in U.S. Pat. No. 2,824,558 to Michael et al; U.S. Pat. No. 4,006,796 to Coehorst; U.S. Pat. No. 4,089,332 to Rose; U.S. Pat. No. 4,244,377 to Grams; U.S. Pat. No. 4,299,237 to Foti; and U.S. Pat. No. 4,060,080 to Akiyama.

OBJECTS AND SUMMARY OF THE INVENTION

Accordingly, it is an object of the present invention to provide an underwater eardrum protector that overcomes the aforementioned problems with the prior art.

It is another object of the present invention to provide an underwater eardrum protector in which means are provided for defining a variable volume chamber, in a cylinder, in fluid communication with an inflatable bladder positioned in the ear, and a piston rod is connected with such means to reduce the volume of the chamber so as to force non-compressible fluid into the bladder.

It is still another object of the present invention to provide such an underwater eardrum protector in which the rod is threadedly engaged with the cylinder to maintain inflation of the bladder.

It is yet another object of the present invention to provide such an underwater eardrum protector in which the rod is connected with the means defining the variable volume chamber in a freely rotatable manner so as to increase the life of such means.

It is a further object of the present invention to provide such an underwater eardrum protector in which the means defining a variable volume chamber includes a piston slidably mounted in the cylinder and having O-rings which provide a seal between the piston and inner cylinder wall such that the freely rotatable connection of the rod to the piston provides axial movement of the O-rings without rotation thereof, so as to prevent rapid wear of the O-rings.

It is a still further object of the present invention to provide such an underwater eardrum protector in which the means defining the variable volume chamber includes a bellows freely rotatably connected to the rod, which is adapted to compress the bellows.

In accordance with an aspect of the present invention, an underwater eardrum protector for use in underwater diving by a person having a perforated eardrum or by a person with a healthy eardrum but not at large water depths includes inflatable bladder means, insertable in an ear canal of the person, for plugging the ear canal; tubing means for supplying a non-compressible fluid into the inflatable bladder means to inflate the inflatable bladder means; and pump means for supplying the non-compressible fluid to the tubing means, the pump means including a cylinder, means defining a variable volume chamber in the cylinder, the chamber being in fluid communication with the tubing means, and rod means for reducing the volume of the chamber so as to force the non-compressible fluid in the chamber through the tubing means and into the inflatable bladder means, the rod means being connected to the means defining the variable volume chamber in a freely rotatable manner and being threadedly connected with the cylinder.

In accordance with another aspect of the present invention, an underwater eardrum protector for use in underwater diving by a person having a perforated eardrum, includes inflatable bladder means, insertable in an ear canal of the person, for plugging the ear canal; tubing means for supplying a non-compressible fluid into the inflatable bladder means to inflate the inflatable bladder means; and pump means for supplying the non-compressible fluid to the tubing means, the pump means including a cylinder having an inner wall, piston means slidable in the cylinder for defining a variable volume chamber with the inner wall of the cylinder, the chamber being in fluid communication with the tubing means, sealing means connected with the piston means for providing a fluid seal between the piston means and the inner wall of the cylinder so as to fluidly seal the chamber, and piston rod means for slidably moving the piston means in the cylinder so as to reduce the volume of the chamber and force the non-compressible fluid in the chamber through the tubing means and into the inflatable bladder means, the piston rod means being connected with the piston means in a freely rotatable manner and being threadedly connected with the cylinder.

In accordance with still another aspect of the present invention, an underwater eardrum protector for use in underwater diving by a person having a perforated eardrum, includes inflatable bladder means, insertable in an ear canal of the person, for plugging the ear canal; tubing means for supplying a non-compressible fluid into the inflatable bladder means to inflate the inflatable bladder means; and pump means for supplying the non-compressible fluid to the tubing means, the pump means including a cylinder, bellows means in the cylinder, the bellows means defining a variable volume chamber therein, the chamber being in fluid communication with the tubing means, and rod means for varying the volume of the chamber so as to force the non-compressible fluid in the bellows through the tubing means and into the inflatable bladder means, the rod means being connected to the bellows means in a freely rotatable manner and being threadedly connected with the cylinder.

The above and other objects, features and advantages of the present invention, will become readily apparent from the following detailed description which is to be read in connection with the accompanying drawings.

DETAILED DESCRIPTION OF THE PREFERRED EMBODIMENTS

Figure 2:
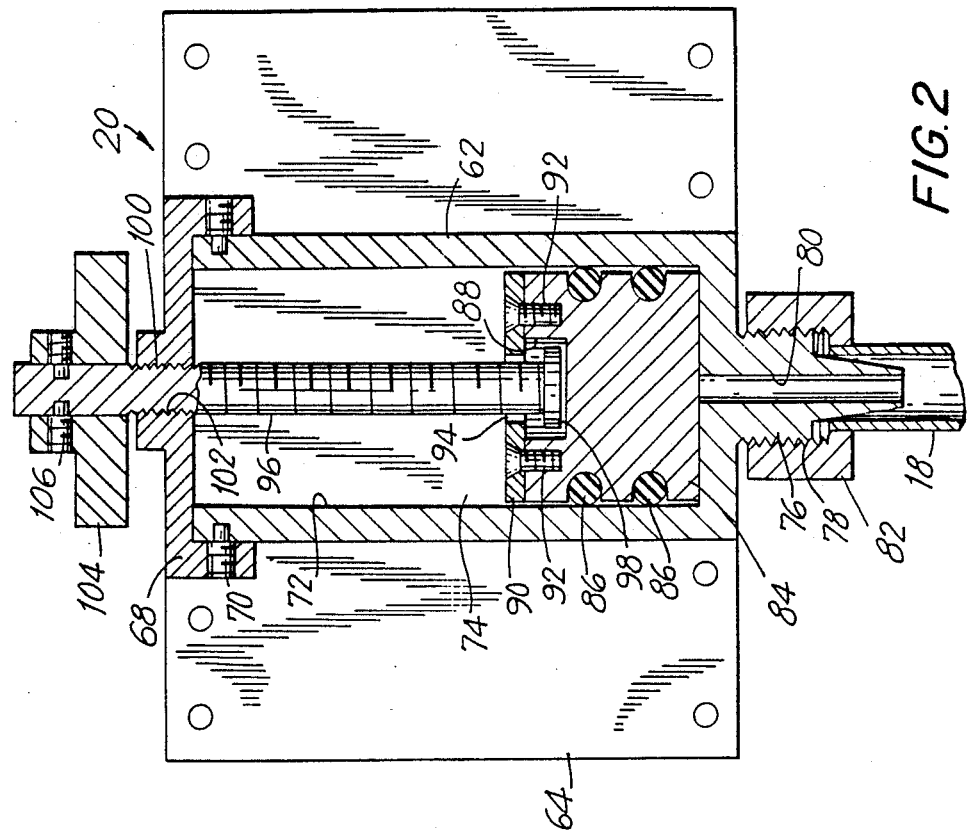
FIG. 2 is an enlarged, partial cross-sectional view of the pump of the underwater eardrum protector of Fig. 1, taken along line 2—2 thereof.
Figure 1:
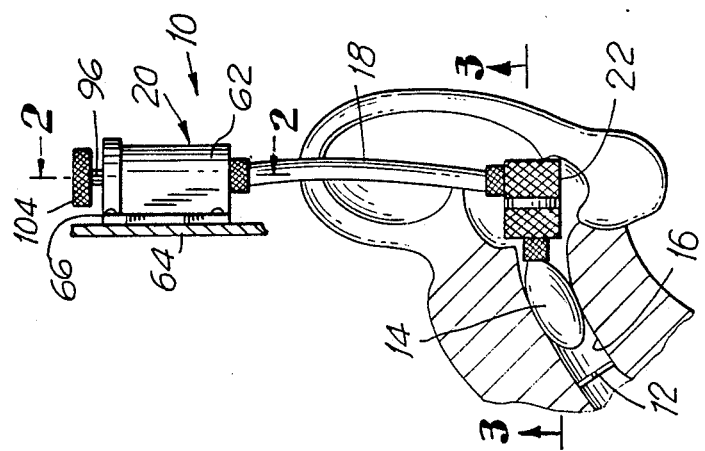
FIG. 1 is a side elevational view of an underwater eardrum protector according to one embodiment of the present invention.
Figure 3:
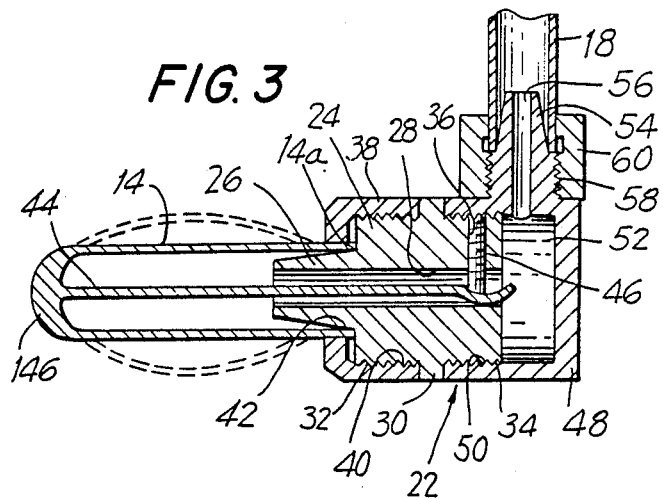
FIG. 3 is an enlarged cross-sectional view of the bladder portion of the underwater eardrum protector of Fig. 1, taken along line 3—3.

Referring to the drawings in detail, and initially to FIGS. 1–3 thereof, an underwater eardrum protector 10 according to a first embodiment of the present invention for use in underwater diving by a person having a perforated eardrum 12, generally includes an inflatable bladder 14 insertable into the ear canal 16 of a person, plastic tubing 18 fluidly connected with inflatable bladder 14 and, pump means 20 for pumping a non-compressible fluid through tubing 18 and into inflatable bladder 14.

Underwater eardrum protector 10 further includes a housing 22 which fluidly connects inflatable bladder 14 with tubing 18. Specifically, as shown in FIG. 3, housing 22 includes a central cylindrical section 24 having a nipple extension 26 axially formed therewith. A central bore 28 extends axially through central cylindrical section 24 and nipple extension 26. In addition, a substantially centrally located radial flange 30 is formed along the outer surface of central cylindrical section 24, with threads 32 and 34 also formed on the outer surface of central cylindrical section 24 on opposite sides of radial flange 30. Finally, a radial bore 36 extends through threads 34 on the outer surface of central cylindrical section 24 and opens into central bore 28, the purpose for which will be readily apparent from the description which follows.

A cup-shaped securing nut 38 having internal threads 40 is threadedly engaged with threads 32 on the outer surface of central cylindrical section 24. Securing nut 38 includes a central bore 42 through which nipple extension 26 extends when securing nut 38 is threadedly secured on central cylindrical section 24. It will be appreciated that flange 30 functions as a stop limit for limiting threaded engagement of securing nut 38 on central cylindrical section 24. In such position, a small gap exists between securing nut 38 and nipple extension 26 extending therethrough.

As shown in FIG. 3, inflatable bladder 14 is formed by a balloon-type, inflatable material and has an open end 14a. A flange of the open end 14A is positioned about nipple extension 26. Thereupon, securing nut 38 is threaded onto threads 32 of central cylindrical section 24 so as to clamp the free end 14a and its flange between nipple extension 26 and securing nut 38 in a fluid sealing manner. Accordingly, the interior of inflatable bladder 14 is in fluid communication with central bore 28.

In addition, as will be made apparent from the description which follows, a semi-rigid or rigid wire 44, string or the like is secured in a sealed manner to distal end 14b of inflatable bladder 14 in any suitable manner and extends through bladder 14 and central bore 28, and is secured against the inner wall which defines central bore 28 by a set screw 46 which is threadedly engaged within radial bore 36 and which extends into central bore 28. Wire 44 provides easy insertion of bladder 14 within ear canal 16 and also limits the axial expansion or inflation of bladder 14 in ear canal 16. As to the latter aspect, the amount of radial inflation of inflatable bladder 14 will vary in dependence upon the position of wire 44. In this regard, wire 44 can be extended from or retracted into central bore 28 and secured at different positions by means of set screw 46.

Figure 5:
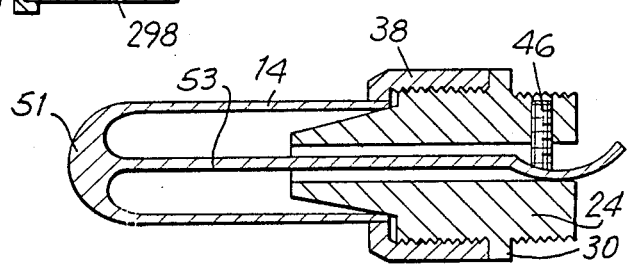
FIG. 5 is an enlarged partial cross-sectional view of the preferred embodiment of the inflatable bladder, similar to FIG. 3 and also taken across line 3—3 of FIG. 1.

In the preferred embodiment, the inflatable bladder with rigid wire 44 can be replaced by an integral rubber balloon with a central rubber rod. This is shown best in FIG. 5. The tip 51 is thicker than the side wall thickness of the inflatable bladder. The control rod 53 is integral with the tip 51 and side walls and it, too, is slightly thicker than the side wall thickness of the inflatable bladder. The end of the rod 53 is secured to the side wall 28 by set screw 36 in the same manner as shown in FIG. 3 and previously described. With this embodiment, inflation of the bladder substantially limits the axial expansion and causes the bladder to substantially expand radially, whereas, in contrast, the device shown in FIG. 3, upon inflation, the control tip is axially limited in expansion yet the areas adjacent to the tip will axially project forwardly.

Housing 22 further includes a tube securing nut 48, also formed in a substantially cup-shape. Tube securing nut 48 is provided with internal threads 50 which engage with threads 34 of central cylindrical section 24 so as to secure tube securing nut 48 thereon. It will be appreciated that, when tube securing nut 48 is secured on central cylindrical section 24 so as to abut against flange 30, an inner fluid chamber 52 is formed therein, in fluid communication with the opposite end of central bore 28.

Tube securing nut 48 further includes a nipple extension 54 which radially extends therefrom. A central bore 56 extends through nipple extension 54 and has one end in fluid communication with inner fluid chamber 52. A portion of the outer surface of nipple extension 54 includes threads 58 thereon. In this manner, one end of tubing 18 is positioned over the non-threaded portion of the outer surface of nipple extension 54, and a nut 60 is threadedly engaged with threads 58 of nipple extension 54 so as to clamp one end or a flange portion of tubing 18 between nipple extension 54 and nut 60 in a fluid sealing manner. In this regard, it will be appreciated that fluid communication is provided between plastic tubing 18 and bladder 14 through central bore 56, inner fluid chamber 52 and central bore 28.

Of course, although the preferred embodiment of the present invention has been described with housing 22 connecting tubing 18 to bladder 14, any other suitable means can be provided for connecting tubing 18 to bladder 14. For example, open end 14a of bladder 14 can be inserted directly over one end of tubing 18 and secured thereat by a suitable clamp, adhesive or the like.

The opposite end of tubing 18 is fluidly connected with pump 20, as best shown in FIG. 2. Specifically, in a first embodiment of the present invention, pump 20 includes a cylinder 62 mounted to a plate 64 by brackets 66. Plate 64 is preferably fastened to either the side of the diver's mask or a special collar around the diver's neck. Cylinder 62 has an open end which is closed by an end cap 68 secured thereto by bolts 70.

Cylinder 62 includes an inner wall 72 that defines a chamber 74 therein. The end of cylinder 62 opposite end cap 68 is formed with a nipple extension 76 having external threads 78 along a portion of the outer surface thereof. A central bore 80 extends through nipple extension 76 and is in fluid communication with chamber 74. In this manner, the opposite end of tubing 18 is positioned over a non-threaded portion of the outer surface of nipple extension 76, and a securing nut 82 is threadedly engaged with thread 78 of nipple extension 76 so as to clamp this opposite end of tubing 18 between nipple extension 76 and securing nut 82 in a fluid sealing manner. In this manner, chamber 74 is fluidly connected with tubing 18.

A piston 84 is slidably positioned in cylinder 62 and is provided with O-rings 86 secured on the outer surface thereof which also engage with inner wall 72 of cylinder 62 so as to provide a fluid sealing arrangement between inner wall 72 and piston 84. It will be appreciated that chamber 74 is a variable volume chamber, the volume of which is dependent upon the position of piston 84 within cylinder 62.

Piston 84 is provided at its upper end with a central cylindrical recess 88. An end plate 90 is secured on the upper surface of piston 84 by bolts 92 and includes a central aperture 94 having a smaller diameter than that of recess 88 so as to partially cover an outer annular portion of recess 88. A piston rod 96 extends through central aperture 94 into recess 88 and includes an end plate 98 having a diameter greater than that of central aperture 94 but less than that of recess 88, and positioned within recess 88. In this manner, piston rod 96 is mechanically connected with piston 84 in a freely rotatable manner.

Piston rod 96 includes external threads 100 thereon. End cap 68 includes a central threaded bore 102 which threadedly engages with threads 100 of piston rod 96. In this manner, rotation of piston rod 96 results in movement of piston rod 96 within cylinder 62. It will be appreciated, as discussed above, that such movement is an axial movement only of the piston, without any rotational movement of piston 84. This results in less wear on O-rings 86 and better water tightness, particularly in situations of deep underwater diving.

From bore 102, piston rod 96 extends out of cylinder 62 and a knob 104 is secured thereon by bolts 106.

As discussed above, current medical practice dictates that a person with a pre-existing ruptured or torn eardrum should not descend deeply in water because of the increased water pressure which could cause water to penetrate into the ear, possibly causing permanent inner ear damage. The present invention solves this problem by blocking water, even at large depths and high water pressure, from passing through the torn or ruptured eardrum. The present invention can also be used, at shallow water depths by all water sport enthusiastis who desire to block water from entering the ear canal, even if there is no health risk to do so.

In operation, inflatable bladder 14 is inserted within ear canal 16. In the initial position, piston 84 is retracted upwardly from the position shown in FIG. 2. Thereafter, the person, above water, rotates knob 104 so as to move piston 84 downwardly in the direction of FIG. 2. Because a non-compressible fluid is provided within chamber 74, this fluid is forced through central bore 80, tubing 18, central bore 56, inner fluid chamber 52 and central bore 28, to inflate bladder 14. This preliminarily secures bladder 14 within ear canal 16 and blocks off any water from entering through the ruptured or torn eardrum. After the diver enters the water and as the diver further descends, he can easily and manually provide any further expansion or contraction of bladder 14 by turning knob 104 which adjusts piston 84 to increase or decrease the pressure of the noncompressible fluid. It will be appreciated that any suitable non-compressible fluid can be used, such as water, alcohol, oil or the like.

It will be appreciated that the present invention is designed only for use at large water depths by people with punctured eardrums. This is because use of the device by a person having a normal non-punctured eardrum at a large depth could result in a punctured eardrum. Specifically, when a person with a normal non-punctured eardrum descends deeply into water, the water pressure on the eardrum, in the absence of the present invention, causes the eardrum to deflect inwardly. To compensate for such inward deflection, an experienced diver equalizes the air pressure by closing off his nose and breathing so that the eustachian tube provides higher pressure air from the chest cavity, through the mouth, nose, and all the way up to the inside of the eardrum. This pushes the eardrum back to its original, non- deflected position. If the underwater eardrum protector according to the present invention is used by a person having a normal, non-punctured eardrum, since it is inserted into the ear canal above water, it will "trap" air between the eardrum and the eardrum protector at one atmosphere of pressure. Then, when equalization is performed and occurs, deflection of the eardrum will go from its normal position to an outwardly deflected position, having a tendency to tear an otherwise good eardrum. This is because the equalization pressure will be more than one atmosphere because the diver is submerged.

Thus, with the present invention, the underwater eardrum protector 10 is inserted into the ear canal 16 prior to descent into water. Since it is intended to be primarily used by people having punctured eardrums at large depths, then the equalized pressure through the eustachian tube will pass all the way through the punctured eardrum to the inflated eardrum protector. In this manner, the present invention can be used by divers with punctured eardrums and provides water tightness of the inner middle ear of the diver.

Figure 4:
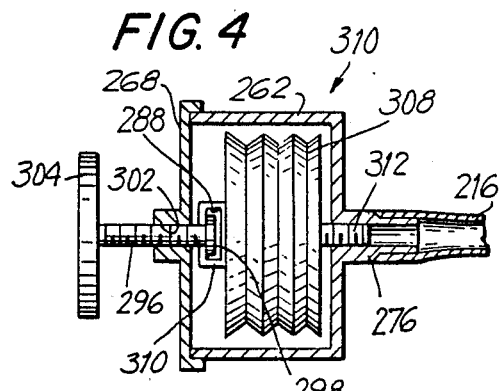
FIG. 4 is a reduced cross-sectional view, similar to that of FIG. 2, of the variable volume chamber portion of an underwater eardrum protector according to a second embodiment of the present invention.

Referring now to FIG. 4, a portion of an underwater eardrum protector 210 according to another embodiment of the present invention will now be described, in which elements corresponding to those identified above with respect to the embodiment of FIGS. 1-3 are identified by the same reference numerals, augmented by 200, and a detailed description thereof will be omitted herein for the sake of brevity.

As shown, a plastic bellows 308 is provided in cylinder 262 and includes an upper extension 310 defining a partially closed recess 288 which accepts end plate 298 at the end of piston rod 296. The opposite end of bellows 308 includes a threaded tube 312 fluidly connected within the variable volume chamber of bellows 308 and which is connected with cylinder 262. Threaded tube 312 exits within nipple extension 276 of cylinder 262.

In this manner, rotation of knob 304 results in compression or expansion of bellows 308 through piston rod 296. As a result, non-compressible fluid within bellows 308 is forced out of or into bellows 308 in order to vary the expansion or contraction of the bladder (not shown and which is identical to that shown in FIG. 3).

Having described specific preferred embodiments of the invention with reference to the accompanying drawings, it will be appreciated that the present invention is not limited to those precise embodiments, and that various changes and modifications can be effected therein by one of ordinary skill in the art without departing from the spirit or scope of the invention as defined by the appended claims.

What is claimed is:

1. An eardrum protector for use in water sports said protector comprising:
   (a) inflatable bladder means, insertable in an ear canal of the person, for plugging the ear canal;
   (b) tubing means for supplying a non-compressible fluid into said inflatable bladder means to inflate said inflatable bladder means; and
   (c) pump means for supplying said non-compressible fluid to said tubing means, said pump means including:
   (i) a cylinder,
   (ii) means defining a variable volume chamber in said cylinder, said chamber being in fluid communication with said tubing means, and
   (iii) rod means for reducing the volume of said chamber so as to force said non-compressible fluid in said chamber through said tubing means and into said inflatable bladder means, said rod means being connected to said means defining the variable volume chamber in a freely rotatable manner and being threadedly connected with said cylinder.

2. An eardrum protector according to Claim 1, further including housing means for fluidly connecting said tubing means to said inflatable bladder means, said housing means including bore means extending therethrough for fluidly connecting said tubing means with said inflatable bladder means, first means for connecting said inflatable bladder means to said housing means in a fluid sealing manner and second means for connecting said tubing means to said housing means in a fluid sealing manner.

3. An eardrum protector according to Claim 2, wherein said first means includes nipple means extendable through an opening in said inflatable bladder means and securing nut means secured to said housing means in surrounding relation to said nipple means so as to clamp said inflatable bladder means between said nipple means and said securing nut means.

4. An eardrum protector according to Claim 2, wherein said second means includes nipple means extended from said housing means into said tubing means and securing nut means connected with said housing means in surrounding relation to said nipple means for clamping said tubing means between said nipple means and said securing nut means.

5. An eardrum protector according to Claim 1, wherein said means defining a variable volume chamber in said cylinder includes piston means slidable in said cylinder for defining said variable volume chamber with said cylinder.

6. An eardrum protector according to Claim 1, wherein said means defining a variable volume chamber in said cylinder includes bellow means in said cylinder, said bellow means being in fluid communication with said tubing means.

7. An eardrum protector according to Claim 1, wherein said inflatable bladder means includes means for limiting expansion of said inflatable bladder means.

8. An eardrum protector according to Claim 7, wherein said means for limiting expansion includes wire means axially positioned within said inflatable bladder means and adjustable to different lengths therein.

9. An eardrum protector according to claim 7, wherein said inflatable bladder means and said means for limiting expansion of said inflatable bladder means are integrally formed.

10. An eardrum protector according to claim 1, wherein the tip of said inflatable bladder is thicker than the side walls of the inflatable bladder.

11. An eardrum protector for use in water sports, said protector comprising:
 (a) inflatable bladder means, insertable in an ear canal of the person, for plugging the ear canal;
 (b) tubing means for supplying a non-compressible fluid into said inflatable bladder means to inflate said inflatable bladder means; and
 (c) pump means for supplying said non-compressible fluid to said tubing means, said pump means including:
  (i) a cylinder having an inner wall,
  (ii) piston means slidable in said cylinder for defining a variable volume chamber with the inner wall of said cylinder, said chamber being in fluid communication with said tubing means,
  (iii) sealing means connected with said piston means for providing a fluid seal between said piston means and the inner wall of said cylinder so as to fluidly seal said chamber, and
  (iv) piston rod means for slidably moving said piston means in said cylinder so as to reduce the volume of said chamber and force said non-compressible fluid in said chamber through said tubing means and into said inflatable bladder means, said piston rod means being connected with said piston means in a freely rotatable manner and being threadedly connected with said cylinder.

12. An underwater eardrum protector according to Claim 11, further including housing means for fluidly connecting said tubing means to said inflatable bladder means, said housing means including bore means extending therethrough for fluidly connecting said tubing means with said inflatable bladder means, first means for connecting said inflatable bladder means to said housing means in a fluid sealing manner and second means for connecting said tubing means to said housing means in a fluid sealing manner.

13. An eardrum protector according to Claim 12, wherein said first means includes nipple means extendable through an opening in said inflatable bladder means and securing nut means secured to said housing means in surrounding relation to said nipple means so as to clamp said inflatable bladder means between said nipple means and said securing nut means.

14. An eardrum protector according to Claim 12, wherein said second means includes nipple means extended from said housing means into said tubing means and securing nut means connected with said housing means in surrounding relation to said nipple means for clamping said tubing means between said nipple means and said securing nut means.

15. An eardrum protector according to Claim 11, wherein said inflatable bladder means includes means for limiting expansion of said inflatable bladder means.

16. An eardurm protector according to claim 15, wherein said inflatable bladder means is integrally formed with said means for limiting expansion of said inflatable bladder means.

17. An eardrum protector as claimed in claim 11 wherein the tip of said inflatable bladder is thicker than the side walls of said inflatable bladder.

18. An eardrum protector according to Claim 15, wherein said means for limiting expansion includes wire means axially positioned within said inflatable bladder means and adjustable to different lengths therein.

19. An eardrum protector according to Claim 11, wherein said sealing means includes at least one O-ring connected between said piston means and said inner wall of said cylinder.

20. An eardrum protector according to Claim 11, wherein said piston means includes a recess therein having a first radial dimension and an end plate secured to said piston means in partial covering relation to said recess, and said piston rod means extends through said end plate into said recess and includes an enlarged end positioned in said recess so as to connect said piston rod means to said piston means in a freely rotatable manner.

21. An eardrum protector according to Claim 11, further including knob means connected with said rod means for rotating said piston means with respect to said cylinder.

22. An eardrum protector for use in water sports, said protector comprising:
 (a) inflatable bladder means, insertable in an ear canal of the person, for plugging the ear canal;
 (b) tubing means for supplying a non-compressible fluid into said inflatable bladder means to inflate said inflatable bladder means; and
 (c) pump means for supplying said non-compressible fluid to said tubing means, said pump means including:
  (i) a cylinder,
  ii) bellows means in said cylinder, said bellows means defining a variable volume chamber therein, said chamber being in fluid communication with said tubing means, and (iii) rod means for varying the volume of said chamber so as to force said non-compressible fluid in said chamber through said tubing means and into said inflatable bladder means, said rod means being connected to said bellows means in a freely rotatable manner and being threadedly connected with said cylinder.

23. An eardrum protector according to Claim 22, further including housing means for fluidly connecting said tubing means to said inflatable bladder means, said housing means including bore means extending therethrough for fluidly connecting said tubing means with said inflatable bladder means, first means for connecting said inflatable bladder means to said housing means in a fluid sealing manner and second means for connecting said tubing means to said housing means in a fluid sealing manner.

24. An eardrum protector according to Claim 23, wherein said first means includes nipple means extendable through an opening in said inflatable bladder means and securing nut means secured to said housing means in surrounding relation to said nipple means so as to clamp said inflatable bladder means between said nipple means and said securing nut means.

25. An eardrum protector according to Claim 23, wherein said second means includes nipple means extended from said housing means into said tubing means and securing nut means connected with said housing means in surrounding relation to said nipple means for clamping said tubing means between said nipple means and said securing nut means.

26. An eardrum protector according to Claim 22, wherein said inflatable bladder means includes means for limiting expansion of said inflatable bladder means.

27. An eardrum protector according to claim 26, wherein said inflatable bladder means is integral with said means for limiting expansion of said inflatable bladder means.

28. An eardrum protector according to claim 22, wherein the tip of said inflatable bladder means is thicker than the side walls of said inflatable bladder means.

29. An eardrum protector according to Claim 26, wherein said means for limiting expansion includes wire means axially positioned within said inflatable bladder means and adjustable to different lengths therein.

30. An eardrum protector according to Claim 22, wherein said bellows means includes an extension having a partially enclosed recess, and said rod means has an enlarged end extending within said partially enclosed recessed for connecting said rod means to said bellow means in a freely rotatable manner.

31. An eardrum protector according to Claim 22, wherein said bellows means is non-rotatably connected with said cylinder.

32. An eardrum protector according to Claim 22, further including knob means connected with said rod means for rotating said piston means with respect to said cylinder.

* * * * *